United States Patent
Zhang et al.

(10) Patent No.: US 10,682,312 B2
(45) Date of Patent: Jun. 16, 2020

(54) METHOD FOR PREPARATION OF HYBRID AMPHIPHILIC STAR COPOLYMER NANO MICELLES

(71) Applicant: JIANGNAN UNIVERSITY, Wuxi, Jiangsu (CN)

(72) Inventors: Liping Zhang, Jiangsu (CN); Caihua Ni, Jiangsu (CN); Ren Liu, Jiangsu (CN); He Liu, Jiangsu (CN); Xinyi Dong, Jiangsu (CN)

(73) Assignee: JIANGNAN UNIVERSITY, Wuxi (CN)

( * ) Notice: Subject to any disclaimer, the term of this patent is extended or adjusted under 35 U.S.C. 154(b) by 105 days.

(21) Appl. No.: 16/159,058

(22) Filed: Oct. 12, 2018

(65) Prior Publication Data
US 2019/0110987 A1    Apr. 18, 2019

(30) Foreign Application Priority Data
Oct. 13, 2017    (CN) .......................... 2017 1 0949726

(51) Int. Cl.
| | | |
|---|---|---|
| *A61K 9/107* | (2006.01) | |
| *C08G 81/00* | (2006.01) | |
| *A61K 31/704* | (2006.01) | |
| *C08G 83/00* | (2006.01) | |
| *C08G 69/10* | (2006.01) | |
| *C08G 69/42* | (2006.01) | |

(52) U.S. Cl.
CPC .......... *A61K 9/1075* (2013.01); *A61K 31/704* (2013.01); *C08G 69/10* (2013.01); *C08G 69/42* (2013.01); *C08G 81/00* (2013.01); *C08G 83/003* (2013.01)

(58) Field of Classification Search
CPC ....... A61K 9/1075; C08G 69/10; C08G 69/42
See application file for complete search history.

(56) References Cited

U.S. PATENT DOCUMENTS

2010/0098761 A1* 4/2010 Song .................. A61K 38/1866
424/486

FOREIGN PATENT DOCUMENTS

AU        2015377981 A     3/2015

OTHER PUBLICATIONS

Yu (Journal of Controlled release; 2015; 205, 89-97).*
Caihua Ni,Geng Wu,Changping Zhu, and Bolong Yao. The Preparation and Characterization of Amphiphilic Star Block Copolymer Nano Micelles Using Silsesquioxane as the Core. J. Phys. Chem. C 2010, 114, 13471-13476.
Caihua Ni,Guangjun Zhu, Changping Zhu,Bolong Yao,D.N.T. Kumar Studies on core-shell structural nano-micelles Based on star block copolymer of poly(lactide) and poly(2-(dimethylamino)ethylmethacrylate) Colloid Polym Sci 2010, 288:1193-1200.
Luyan Wu, Caihua Ni, Liping Zhang & Gang Shi.Preparation of pH-sensitive zwitterionic nano micelles and drug controlled release for enhancing cellular uptake. Journal of Biomaterials Science, Polymer Edition. 2016, 27 (7), 643-656.
Liping Zhang, Luyan Wu, Yuanlong Cao, Yunan Wu, Jing Chen & Caihua Ni. Studies on preparations and pH/redoxresponsiveness of zwitterionic nanomicelles of poly[lysine-co-N,N-bis(acryloyl)cystamine-co-dodecylamine]. International Journal of Polymeric Materials and Polymeric Biomaterials. 2018, 67(8), 528-534.
Liping Zhang, Luyan Wu, Gang Shi, Xinxin Sang & Caihua Ni, Studies on the preparation and controlled release of redox/pH-responsive zwitterionic nanoparticles based on poly-L-glutamic acid and cystamine, Journal of Biomaterials Science, Polymer Edition. 2018. 29(6), 646-662.
Caihua Ni,Guifeng Ni et al.The preparation of inorganic/organic hybrid nanomaterials Containing silsesquioxane and its reinforcement for an epoxy resin network. Colloid Polym Sci 2010, 288:469-477.
Zhiqiang Xu, Caihua Ni , Bolong Yao , Lei Tao, Changping Zhu, Qingbang Han, Jiaquan Mi. The preparation and properties of hybridized hydrogels based on cubic thiol-functionalized silsesquioxane covalently linked with poly (N-isopropylacrylamide). Colloid Polym Sci 2011, 289:1777-1782.

* cited by examiner

*Primary Examiner* — Pancham Bakshi
(74) *Attorney, Agent, or Firm* — Enshan Hong; VLP Law Group LLP

(57) ABSTRACT

Hybrid amphiphilic star copolymer nano micelles are prepared in the invention. Cage shaped octa(γ-aminopropyl) silsesquioxanes is selected as the inorganic part, and L-glutamic benzyl ester—five membered ring anhydride is ring-opening polymerized by the initiation of amino groups on the surface of cage shaped octa(γ-aminopropyl) silsesquioxanes, producing copolymers with cage shaped octa(γ-aminopropyl) silsesquioxanes as nucleus and poly (L-glutamic-benzyl ester) as arms. The copolymers reacts with monomethoxy poly (ethylene glycol) carboxylic acid by condensation. Finally, the benzyl groups in the side chains of poly (L-glutamic acid-benzyl ester) are converted into hydrazine groups by acylhydrazination to obtain hybrid amphiphilic star copolymer nano micelles. The micelles can load doxorubicin, they are safe to human body and have good application prospects.

9 Claims, 3 Drawing Sheets

Figure 1 (As abstract Figure)

US 10,682,312 B2

METHOD FOR PREPARATION OF HYBRID AMPHIPHILIC STAR COPOLYMER NANO MICELLES

CROSS-REFERENCES TO RELATED APPLICATIONS

This application claims priority from China Patent Application Serial Number 2017109497263 which was filed on Oct. 13, 2017.

BACKGROUND OF THE INVENTION

1. Technical Field

The invention relates to the technical field of biomedical materials, in particular to methods for preparation of inorganic/organic hybrid star-shaped copolymer nano micelles.

2. Background Art

Polymeric nano micelles as chemotherapeutic drug carriers have shown bright prospects in the field of cancer treatment. The injection-type nano micelles can pass through some barriers of the body tissues and reach the tumor site with the blood circulation, thus release the drug at the lesion site, greatly improve the bioavailability of the drug and reduce the toxicity and side effects. It is of great significance in both theory and application to develop nano-micelle drug carriers with regular structure, controllable size, targeted delivery and controlled release features.

Usually, the method for preparation of nano micelles through self-assembly of linear amphiphilic copolymers is one of the most studied strategies. However, the linear copolymer multimolecular nano micelles are unstable in dilute solutions and will dissociate into monomolecules having no ability for drug-loading. At the same time, drug loading only by physical interaction is instable, resulting in drug leakage, sudden release, efficacy reduction and other problems.

In recent years, star copolymer nano micelles have attracted much attention due to their advantages such as stability, narrow particle size distribution, easy modification and reducing sudden release.

Cage shaped silsesquioxanes (POSS) have attracted some scholars' attention because of their advantages in preparation of polymers with regular structures. POSS is a kind of nano-scale three-dimensional system with a diameter of 1-3 nm and an internal framework of Si—O bonds and an external organic group. At present, the application of hybrid materials containing POSS in the field of medical materials has shown bright prospects and attracted many scholars' interest. As the core of star polymer, POSS has the following prominent advantages: (1) good biocompatibility; (2) highly symmetrical structure, its rigid cage skeleton can lead to a formation of stable monomolecular nano micelle; (3) can be further functionalized to produce multi-arms, which is beneficial for increase of drug loading; (4) stable performance, resistance to high temperatures, good mechanical strength; (5) small particle size and easy excretion; (6) simple synthetic conditions for preparation, good monodispersity.

Polyamino acids are biodegradable materials with good biocompatibility, non-toxic, no side effects and no immunogenicity to bodies; they can be hydrolyzed or enzymatic hydrolyzed in vivo into small molecules which are absorbed or excreted by the human body. The side chains of polyglutamic acid and polyaspartic acid have pendant carboxyl groups which are easily modified and covalently drug loaded. Therefore, they are often employed to prepare nano micelles.

At present, most of drug release curves still show some problems such as too fast at the initial stage and too slow at the later stage. The main reason for sudden release is the simple physical way for drug loading. Some cross-linking bonds are insensitive to weak acidic environment around the tumor, and it is difficult to control the release by pH values. Some micelles are pH sensitive, but they are also disintegrated under acid stimulation, and instability occurs. All these factors will lead to uneven drug release rate.

SUMMARY OF THE INVENTION

In order to solve the above technical problems, the aim of the present invention is to provide a method for preparation of hybrid amphiphilic star copolymer nano micelles.

Firstly, cage shaped octa(γ-aminopropyl) silsesquioxanes was selected as the inorganic part of the hybrid amphiphilic star copolymer. It was expected that the regularly structured nano micelles could be obtained by the dominant role of the cage skeleton of cage shaped octa(γ-aminopropyl) silsesquioxanes in the synthetic process.

Secondly, L-glutamic benzyl ester was transformed into L-glutamic benzyl ester—five membered ring anhydride under the action of triphosgene. The reaction was carried out in a water bath and gradually heated to 45° C., after the benzyl ester was dissolved, triphosgene was added to the reaction solution. The clear and transparent solution was obtained after 5 hours reaction under the protection of N2. The product was precipitated by excessive anhydrous petroleum ether, then purified by tetrahydrofuran/anhydrous petroleum ether. L-glutamic benzyl ester—five membered ring anhydride (NCA) was obtained after vacuum drying at 35° C.

Next, L-glutamic benzyl ester—five membered ring anhydride (NCA) experienced a ring-opening polymerization by the initiation of amino groups on the surface of the cage shaped octa(γ-aminopropyl) silsesquioxanes, and an inorganic/organic hybrid copolymer with cage shaped octa(γ-aminopropyl) silsesquioxanes as the nucleus and poly-L-glutamic benzyl ester as the arms was formed. Specifically, in a three-necked flask containing anhydrous dichloromethane as solvent, cage shaped octa(γ-aminopropyl) silsesquioxanes was added, and L-glutamic benzyl ester—five membered ring anhydride was added after dissolution. The reaction was carried out for 48 hours under stirring at 25° C. and nitrogen protection. The intermediate product, labeled as Si-PBLG, was precipitated with anhydrous petroleum ether and washed several times with distilled water. Finally, the product was dried for 48 h in a vacuum condition.

Then, a condensation reaction between the intermediate product Si-PBLG and monomethoxy polyethylene glycol carboxylic acid took place. Specifically, a small amount of 1-(3-dimethylaminopropyl)-3-ethylcarbodiimide hydrochloride and N-hydroxy succinimide were added as catalysts for the condensation reaction of the amino groups at the end of poly (L-glutamic benzyl ester) with the carboxyl groups of monomethoxy polyethylene glycol carboxylic acid. The condensation reaction was carried out at 50° C. and precipitated by ethyl ether. The hybrid amphiphilic star copolymer was obtained after dissolving, dialysing and freeze-drying.

Finally, the side chain of poly (L-glutamic benzyl ester) was converted into hydrazide group by an acylhydrazination reaction. Specifically, the hybrid amphiphilic star copolymer, hydrazine hydrate solution and 1,4-dioxane were added to a reaction flask in turn. After refluxing at 40° C. for 5 h, the reaction solution was transferred into a dialysis bag for dialyzing 48 h under the condition of avoiding light, and the hybrid amphiphilic star copolymer nano micelles were obtained.

Free amino group in hydrazide group can form —N=C— bond with carbonyl group in doxorubicin. Under the stimulation of acidic condition —N=C— double break, leading to controlled release of the drug, which solves the problem of acid sensitivity of nanomicelles.

The invention also prepares doxorubicin-loaded hybrid amphiphilic star-shaped copolymer nano micelles. Specifically, a powder sample is obtained by freeze-drying any of the nano micelle solutions. The sample is added to excessive doxorubicin dimethyl sulfoxide solution and a small amount of triethylamine is added to neutralize hydrochloric acid in doxorubicin hydrochloride, stirring at room temperature for 24 hours, free doxorubicin on the micelle surface was removed by dialysis in deionized water, and the drug-loaded hybrid amphiphilic star copolymer nano micelles were obtained after freeze-drying.

The advantages of the invention are:

1. Using cage shaped octa(γ-aminopropyl) silsesquioxanes as inorganic part and the nucleus of the hybrid amphiphilic star copolymer, L-glutamic benzyl ester—five membered ring anhydride was polymerized through a ring-opening polymerization with surface amino groups as initiation agents, resulting in nano micelles with regular structure, controllable size and stable performance of the product, thus enhancing the properties of nano micelles.

2. Nano micelles were formed by self-assembly of hydrophobic and hydrophilic segments. Poly (L-glutamic-benzyl ester) was used as the inner layer and polyethylene glycol (PEG) as the outer layer of nanomicelles. The micellar structure is stable.

3. Acylhydrazine groups in the nano micelles can form covalent bonds with doxorubicin, which improves drug-loading stability, reduces drug leakage and drug burst release.

4. All materials have good biocompatibility and are safe to human body. The product has applied prospects.

DESCRIPTION OF PREFERRED EMBODIMENTS

Figure 1:
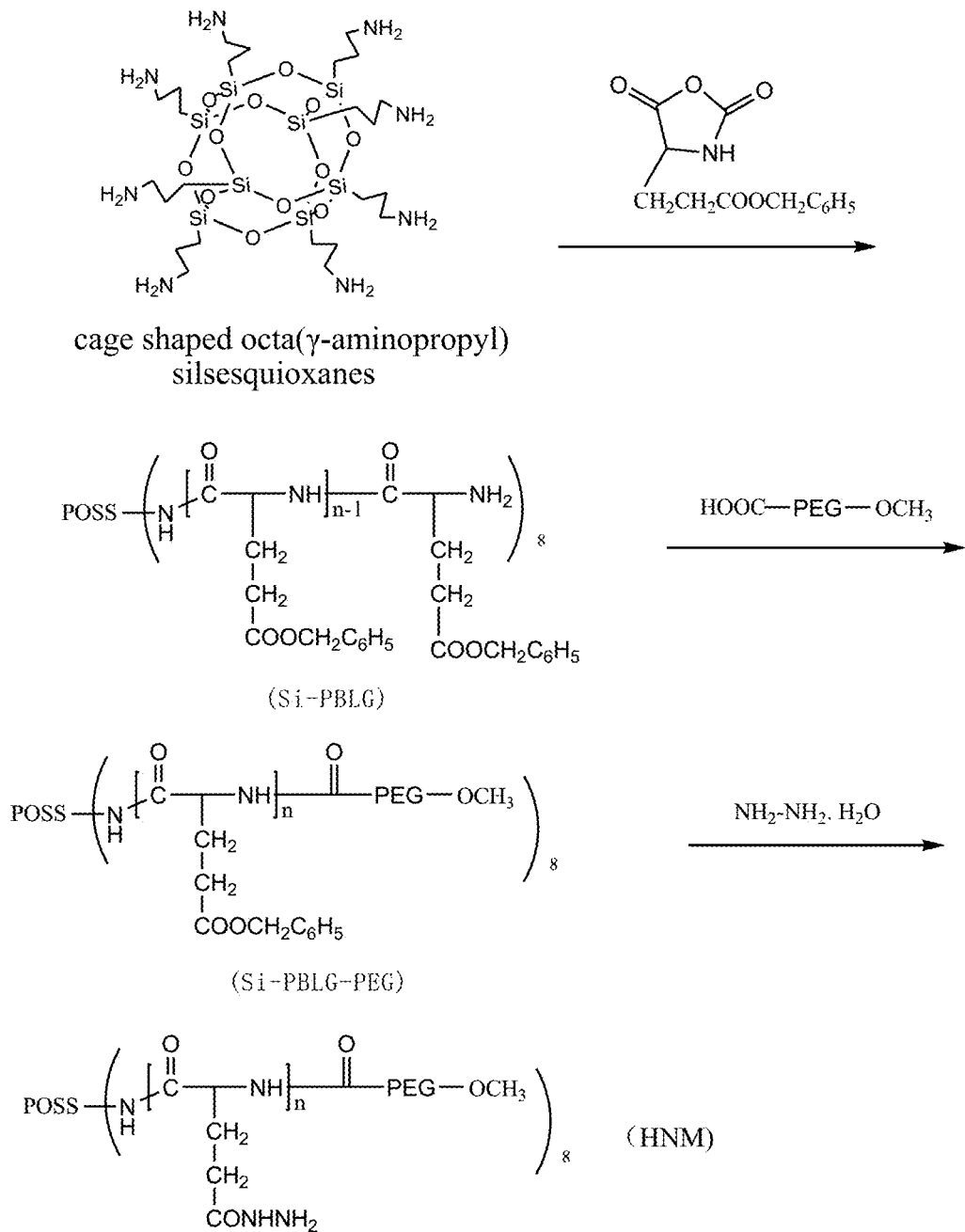
FIG. 1 is a schematic diagram of synthesis of hybridized amphiphilic star copolymer nano micelles.

The detailed implementation of the invention is further described as follows. The following embodiments are used to illustrate the invention, but not to limit the scope of the invention.

Example 1

Firstly, L-glutamic benzyl ester was synthesized: L-glutamic acid 40 g and benzyl alcohol 33 g were placed in 250 mL flask, mixing uniformly with magnetic stirring. The reaction temperature increases slowly to 70° C., adding 60% sulfuric acid 45 g, until the solution was clear after 30 mins. The solution was distillated under reduced pressure, then the reaction solution was poured into NaHCO$_3$ solution for neutralizing the acid; the product was cooled at 4° C. for 24 hours and extracted by filtration under reduced pressure. A white flaky solid, L-glutamic benzyl ester, was obtained after washing with ethanol and distilled water, recrystallization in 5% ethanol solution at 70° C., cooling at 4° C. overnight, filtration and drying at 35° C. for 48 h.

Preparation of L-glutamic benzyl ester—five membered ring anhydride: L-glutamic benzyl ester 6.1 g was added to a three-necked flask with 60 mL of tetrahydrofuran, and the benzyl ester was gradually dissolved when heated to 45° C. in a water bath, triphosgene 8.4 g was added to the solution, the reaction was carried out for 5 hours under the protection of N2, and the reacting solution became transparent; the remaining HCl gas and phosgene produced in the reaction were driven out by continuous entry of N2, the reaction solution was slowly added to the excess anhydrous petroleum ether, the white needle like crystal was obtained in an ice bath, the product was purified by tetrahydrofuran/anhydrous petroleum ether and was separated through filtration; finally, the product L-glutamic benzyl ester—five membered ring anhydride was obtained after vacuum drying at 35° C., the product was marked as NCA.

Ring-opening polymerization: Cage shaped octa(γ-aminopropyl) silsesquioxanes 2.22 g was added into a three-necked flask containing anhydrous dichloromethane as a solvent, and L-glutamic benzyl ester—five membered ring anhydride 26.3 g was added to the flask for the reaction under protection of N2 and stirring for 48 h at 25° C., The NCA ring-opening polymerization was initiated by surface amino groups of cage shaped octa(γ-aminopropyl) silsesquioxanes, the copolymeric product was precipitated by anhydrous petroleum ether, washed several times with distilled water, and then dried in vacuum for 48 h, the intermediate product was labeled as Si-PBLG.

Condensation reaction: The above intermediate product Si-PBLG was dissolved in chloroform 50 g in a reaction bottle, then monomethoxy polyethylene glycol carboxylic acid 5 g, coded name as CH3O-PEG-COOH, was added in a certain proportion, and a small amount of 1-(3-dimethylamino propyl)-3-ethylcarbodiimide hydrochloride 2 g and N-hydroxy succinimide 1 g were added as catalysts for the condensation reaction at 50° C.; the hybrid amphiphilic star copolymer, labeled as Si-PBLG-PEG, was obtained after precipitation by ether, re-dissolution, dialysis and freeze-drying.

Acylhydrazination reaction: The hybrid amphiphilic star copolymer Si-PBLG-PEG 12 g, hydrazine hydrate solution 5 g and 1,4-dioxane 5 mL were added in a three-necked flask in turn; after refluxing reaction at 40° C. for 5 h, the reaction solution was transferred into a dialysis bag with cutoff molecular weight of 3500, dialyzed for 48 h avoiding light, and the hybrid amphiphilic star copolymer nano micelles were obtained, marked as HNM-1.

The schematic diagram of synthesis of hybridized amphiphilic star copolymer nano micelles was showed in FIG. 1.

Example 2

Similar to the example 1, but the weight of L-glutamic benzyl ester—five membered ring anhydride (NCA) was changed to 32.9 g, and the remaining steps were unchanged, HNM-2 was synthesized.

Example 3

Similar to the example 1, but the weight of L-glutamic benzyl ester—five membered ring anhydride (NCA) was changed to 39.5 g, and the remaining steps were unchanged, HNM-3 was synthesized.

Example 4

Similar to the example 1, but the weight of L-glutamic benzyl ester—five membered ring anhydride (NCA) was changed to 46.1 g, and the remaining steps were unchanged, HNM-4 was synthesized.

Example 5

Similar to the example 1, but the weight of L-glutamic benzyl ester—five membered ring anhydride (NCA) was changed to 52.6 g, and the remaining steps were unchanged, HNM-5 was synthesized.

Example 6

Similar to the example 1, but the weight of monomethoxy polyethylene glycol carboxylic acid was changed to 10 g, and the remaining steps were unchanged, HNM-6 was synthesized.

Example 7

Similar to the example 1, but the weight of monomethoxy polyethylene glycol carboxylic acid was changed to 20 g, and the remaining steps were unchanged, HNM-7 was synthesized.

Example 8

Similar to the example 1, but the weight of hydrazine hydrate solution was changed to 6 g, and the remaining steps were unchanged, HNM-8 was synthesized.

Example 9

Similar to the example 1, but the weight of hydrazine hydrate solution was changed to 7.5 g, and the remaining steps were unchanged, HNM-9 was synthesized.

Example 10

Figure 2:
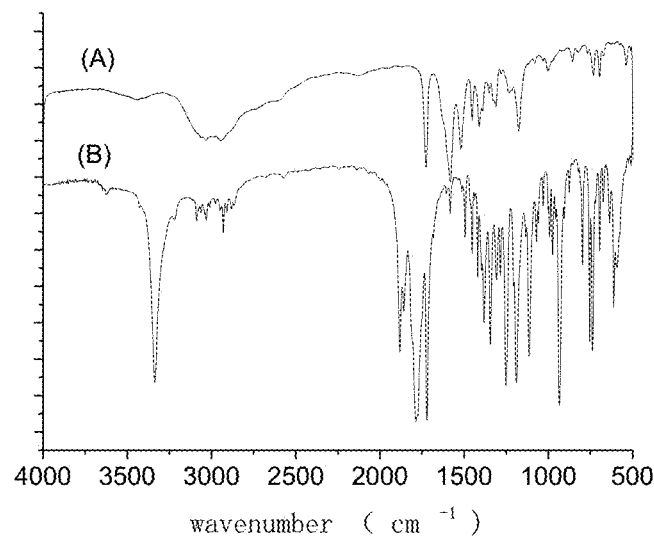
FIG. 2 shows IR spectra of monomers: (A) L-glutamic-benzyl ester; (B) L-glutamic benzyl ester—five membered ring anhydride.

The monomers of L-glutamic benzyl ester and L-glutamic benzyl ester—five membered ring anhydride were characterized by infrared spectroscopy using KBr tablet method. The wavenumber ranged from 4000 cm-1 to 500 cm-1 and the resolution was 4 cm-1. The results were shown in FIG. 2.

In curve (A), the absorption peaks at 1665 cm-1, 770 cm-1 and 691 cm-1 correspond to the out-of-plane deformation vibration absorption of benzene rings and their single substituted absorption, respectively. The absorption peak at 1710 cm-1 correspond to the carbonyl absorption on benzyl esters, indicating that BLG has been successfully synthesized; in curve (B), new absorptions occurs at 1785 cm-1 and 1753 cm-1. The peaks correspond to the two carbonyl groups on the five-membered ring of BLG-NCA. The absorption peaks shift to high frequency because of the vibration coupling, which indicates that BLG-NCA has been successfully synthesized.

Example 11

Figure 3:
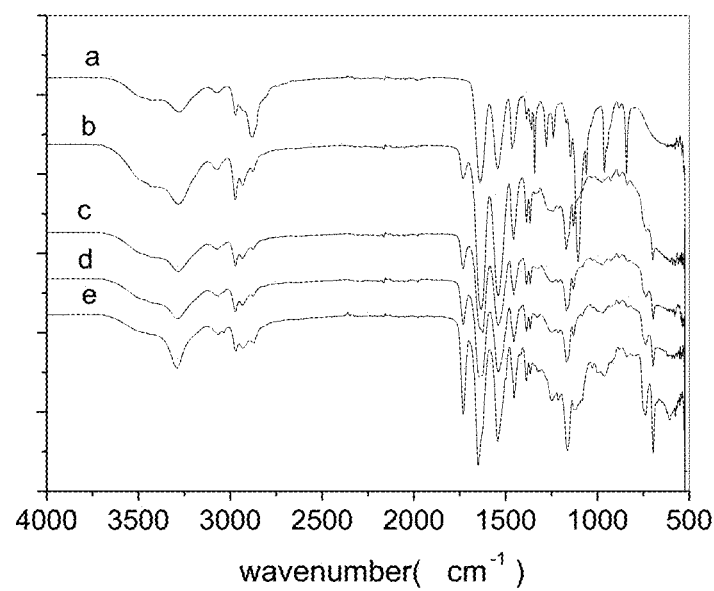
FIG. 3 shows IR spectra of the hybrid amphiphilic star copolymer nano micelles, a: HNM-1; b: HNM-2; c: HNM-3; d: HNM-4 and e: HNM-5.

The hybrid amphiphilic star copolymer nano micelle sample solutions HNM-1, HNM-2, HNM-3, HNM-4 and HNM-5 from embodiments 1, 2, 3, 4 and 5 were freeze-dried, and was characterized by infrared spectroscopy using the same method as described above. The results were shown in FIG. 3.

It could be seen from the Figure that the new appeared at 2878 cm-1 and 2960 cm-1 were stretching vibration absorption peaks of carbon-hydrocarbon in CH2, and the peaks at 1098 cm-1 and 1160 cm-1 were ascribed to stretching vibration absorption of C—O—C ether bonds, indicating that the polyethylene glycol component was involved in the copolymer, which proved the synthesis was successful.

Example 12

Figure 4:
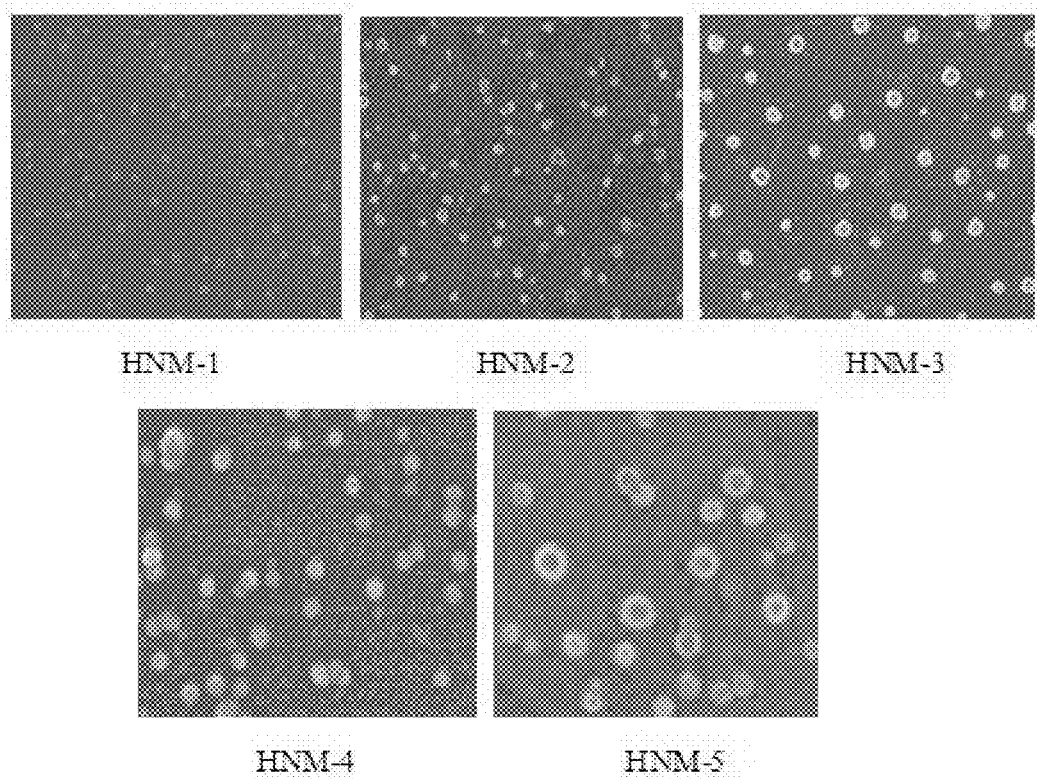
FIG. 4 shows scanning electron microscope of the hybridized amphiphilic star copolymer nano micelles.

Observation of the morphologies of nano micelles: The samples of hybrid amphiphilic star-shaped copolymer nano micelles of HNM-1, HNM-2, HNM-3, HNM-4 and HNM-5 from the above examples 1, 2, 3, 4 and 5 were dried on copper mesh, and the surface of the micelles was sprayed with gold after drying at room temperature. The voltage was adjusted to 1 kV and the morphology and dispersion of micellar particles were observed in a high vacuum environment. The results are shown in FIG. 4. The nano micelles were regular and spherical, and the diameters of HNM-1, HNM-2, HNM-3, HNM-4 and HNM-5 increased sequentially.

Example 13

Figure 5:
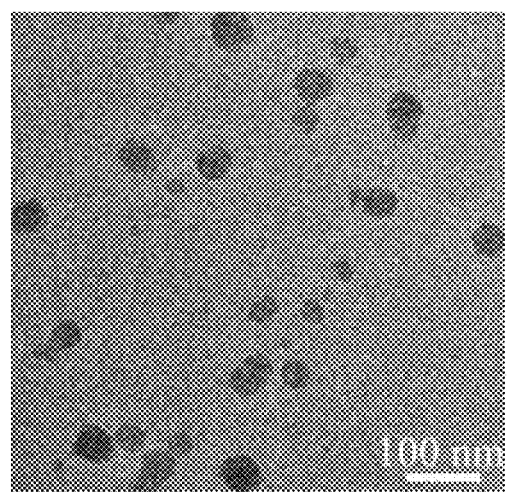
FIG. 5 The transmission electron microscopy of the drug-loaded hybridized amphiphilic star copolymer nano micelles.

Preparation of drug-loaded hybrid amphiphilic star-shaped copolymer nano micelles: firstly the hybrid amphiphilic star copolymer micelles HNM-1 were prepared according to the method described in example 1, and the powder sample is obtained by freeze-drying of any of the nano micelle solutions; the dried powder sample 20 mg was added to an excess dimethyl sulfoxide solution containing doxorubicin hydrochloride with a concentration of 2 mg/mL, a small amount of triethylamine was added to the solution for neutralizing hydrochloric acid in doxorubicin hydrochloride; the free doxorubicin on the surface of the nano micelles were removed by dialysis in deionized water at room temperature for 24 hours, the drug-loaded hybrid amphiphilic star copolymer nano micelles were obtained after freeze-drying. Its morphology was shown in FIG. 5. After drug loading, the morphology was still spherical and slightly increased in size.

The above description is only a preferred method of implementation of the invention and is not used to limit the invention. It should be noted that, for ordinary technical personnel in the field of technology, some improvements and variations can be made under the technical principles of the invention. These improvements and variations should also be considered as the scope of protection of the invention.

What is claimed is:

1. A method of preparing hybrid amphiphilic star copolymer micelles comprising:

(1) preparing monomers by:
mixing L-glutamic benzyl ester with tetrahydrofuran to form a mixture,
heating the mixture and dissolving L-glutamic benzyl ester in the tetrahydrofuran to form a solution,
adding triphosgene to the solution to carry out a reaction under protection of $N_2$ until the solution becomes transparent,
driving out HCl gas and phosgene produced in the reaction with continuous entry of $N_2$,
adding the transparent solution to anhydrous petroleum ether in excess amount and obtaining white needle like crystal product in an ice bath,
purifying the white needle like crystal product with tetrahydrofuran and/or anhydrous petroleum ether to obtain a purified product,
isolating the purified product through filtration to obtain an isolated product, and
vacuum drying the isolated product to obtain L-glutamic benzyl ester—five membered ring anhydride (NCA);

(2) ring-opening polymerizing of NCA by:
mixing and stirring cage shaped octa(γ-aminopropyl) silsesquioxanes, anhydrous dichloromethane and the L-glutamic benzyl ester—five membered ring anhydride obtained in step (1) under protection of $N_2$ to initiate ring-opening polymerization and obtain a copolymeric product, and
isolating, washing, and drying the copolymeric product (labeled as Si-PBLG);

(3) conducting condensation reaction by:
dissolving the Si-PBLG obtained in step (2) in chloroform to obtain dissolved Si-PBLG,
reacting the dissolved Si-PBLG with monomethoxy polyethylene glycol carboxylic acid (coded as $CH_3O$-PEG-COOH) in presence of 1-(3-dimethylamino propyl)-3-ethylcarbodiimide hydrochloride and N-hydroxy succinimide as catalysts to obtain a hybrid amphiphilic star copolymer (labeled as Si-PBLG-PEG), and
purifying the Si-PBLG-PEG by precipitation with ether, re-dissolution, dialysis, and freeze-drying to obtain purified Si-PBLG-PEG;

(4) conducting acylhydrazination reaction by:
mixing the purified Si-PBLG-PEG obtained in step (3) with hydrazine hydrate solution and 1,4-dioxane and carrying out a refluxing reaction to obtain a reaction solution, and
dialyzing the reaction solution to obtain the hybrid amphiphilic star copolymer nano micelles.

2. The method of claim 1 wherein in step (2), molar ratio of cage shaped octa(γ-aminopropyl) silsesquioxanes to L-glutamic benzyl ester—five membered ring anhydride is 1:40, 1:50, 1:60, 1:70, or 1:80, and the corresponding hybrid amphiphilic star copolymer nano micelles so obtained are labeled as HNM-1, HNM-2, HNM-3, HNM-4 and HNM-5, respectively.

3. The method of claim 1 wherein in step (3), number-average molecular weight of monomethoxy polyethylene glycol carboxylic acid is 620.

4. The method of claim 1, wherein in step (3), weight ratio of Si-PBLG to monomethoxy polyethylene glycol carboxylic acid is 1:0.5, 1:1, or 1:2.

5. The method of claim 1, wherein in step (3), weight ratio of 1-(3-dimethylaminopropyl)-3-ethylcarbodiimide hydrochloride to N-hydroxy succinimide is 2:1, and combined weight of the two makes up 30% of the weight of Si-PBLG.

6. The method of claim 1, wherein in step (4), weight ratio of the hybrid amphiphilic star copolymer Si-PBLG-PEG to the hydrazine hydrate solution is 2.4:1~1.6:1.

7. The method of claim 1, wherein in step (4), concentration of the hydrazine hydrate solution is 80%.

8. The method of claim 1, wherein in step (4), volume of 1,4-dioxane is the same as the hydrazine hydrate solution.

9. A method for preparing drug-loaded hybrid amphiphilic star-shaped copolymer nano micelles comprising:
1) freeze drying hybrid amphiphilic star copolymer micelles prepared based on claim 1 to obtain dried powder,
2) adding the dried powder to an excess dimethyl sulfoxide solution containing doxorubicin hydrochloride to obtain a first mixture,
3) adding triethylamine to the first mixture obtained in step 2) for neutralizing hydrochloric acid in doxorubicin hydrochloride to obtain a second mixture containing nano micelles,
4) removing free doxorubicin on the surface of the nano micelles by dialysis in deionized water at room temperature to obtain a third mixture, and
5) freeze drying the third mixture of step 4) to obtain the drug-loaded hybrid amphiphilic star copolymer nano micelles.

* * * * *